United States Patent
Shapland et al.

(10) Patent No.: US 8,292,871 B2
(45) Date of Patent: Oct. 23, 2012

(54) REGIONAL CARDIAC TISSUE TREATMENT

(75) Inventors: James Edward Shapland, Vadnais Heights, MN (US); Tuan Minh Doan, Burnsville, MN (US); David Martin Kaye, Beaumaris (AU); Adam Lucas Bilney, Wy Yung (AU); Melissa Jane Byrne, Melbourne (AU)

(73) Assignee: Osprey Medical, Inc., Eden Prairie, MN (US)

( * ) Notice: Subject to any disclaimer, the term of this patent is extended or adjusted under 35 U.S.C. 154(b) by 0 days.

(21) Appl. No.: 12/799,007

(22) Filed: Apr. 14, 2010

(65) Prior Publication Data

US 2010/0274173 A1 Oct. 28, 2010

Related U.S. Application Data

(63) Continuation of application No. 11/490,476, filed on Jul. 20, 2006, now Pat. No. 7,722,596, which is a continuation-in-part of application No. PCT/AU2005/000237, filed on Feb. 23, 2005.

(60) Provisional application No. 60/612,846, filed on Sep. 24, 2004, provisional application No. 60/548,038, filed on Feb. 26, 2004.

(51) Int. Cl.
*A61M 31/00* (2006.01)
*A61M 29/00* (2006.01)
*A61B 19/00* (2006.01)

(52) U.S. Cl. ..... 604/509; 604/500; 604/508; 604/96.01; 128/898

(58) Field of Classification Search ............... 604/500, 604/509, 508, 96.01; 128/898
See application file for complete search history.

(56) References Cited

U.S. PATENT DOCUMENTS

| | | | |
|---|---|---|---|
| 4,054,137 | A | 10/1977 | Lee et al. |
| 4,581,017 | A | 4/1986 | Sahota |
| 4,795,427 | A | 1/1989 | Helzel |
| 4,969,470 | A | 11/1990 | Mohl et al. |
| 5,338,662 | A | 8/1994 | Sadri |
| 5,423,745 | A | 6/1995 | Todd et al. |
| 5,494,822 | A | 2/1996 | Sadri |
| 5,807,318 | A | 9/1998 | St. Goar et al. |
| 5,807,322 | A | 9/1998 | Lindsey et al. |
| 5,810,757 | A | 9/1998 | Sweezer, Jr. et al. |

(Continued)

FOREIGN PATENT DOCUMENTS

DE 10102045 A1 1/2003

(Continued)

OTHER PUBLICATIONS

Alfayoumi, F. et al., "The No-Reflow Phenomenon: Epidemiology, Pathophysiology, and Therapeutic Approach," *Reviews in Cardiovascular Medicine*, vol. 6, No. 2, pp. 72-83 (2005).

(Continued)

*Primary Examiner* — Christopher D Koharski
*Assistant Examiner* — Ian Holloway
(74) *Attorney, Agent, or Firm* — Merchant & Gould PC (57) ABSTRACT

A method for treating an occlusion in a coronary artery of a patient includes percutaneously advancing an occlusion treatment tool (such as an angioplasty balloon or stent delivery device) through the vasculature of the patient and into a coronary artery to a site of the occlusion. Following the treatment of the occlusion, a therapeutic agent is admitted into the first coronary artery. The therapeutic agent is selected to treat microvasculature obstructions at a target cardiac tissue site distal to the site of the occlusion.

20 Claims, 5 Drawing Sheets

U.S. PATENT DOCUMENTS

| | | | |
|---|---|---|---|
| 5,813,842 | A | 9/1998 | Tamari |
| 5,871,464 | A | 2/1999 | Tryggvason et al. |
| 5,871,465 | A | 2/1999 | Vasko |
| 6,021,340 | A | 2/2000 | Randolph et al. |
| 6,080,170 | A | 6/2000 | Nash et al. |
| 6,093,392 | A | 7/2000 | High et al. |
| 6,110,139 | A | 8/2000 | Loubser |
| 6,152,141 | A * | 11/2000 | Stevens et al. ............... 128/898 |
| 6,186,146 | B1 | 2/2001 | Glickman |
| 6,254,563 | B1 | 7/2001 | Macoviak et al. |
| 6,295,990 | B1 * | 10/2001 | Lewis et al. .................. 128/898 |
| 6,342,214 | B1 | 1/2002 | Tryggvason et al. |
| 6,376,471 | B1 | 4/2002 | Lawrence, III et al. |
| 6,398,752 | B1 | 6/2002 | Sweezer et al. |
| 6,500,158 | B1 | 12/2002 | Ikeguchi |
| 6,508,777 | B1 * | 1/2003 | Macoviak et al. .......... 604/4.01 |
| 6,554,819 | B2 | 4/2003 | Reich |
| 6,558,349 | B1 | 5/2003 | Kirkman |
| 6,569,147 | B1 * | 5/2003 | Evans et al. .................. 604/509 |
| 6,585,716 | B2 | 7/2003 | Altman |
| 6,595,963 | B1 | 7/2003 | Barbut |
| 6,638,264 | B1 | 10/2003 | Tryggvason et al. |
| 6,638,268 | B2 | 10/2003 | Niazi |
| 6,673,039 | B1 | 1/2004 | Bridges et al. |
| 6,689,090 | B1 | 2/2004 | Tryggvason et al. |
| 6,699,231 | B1 | 3/2004 | Sterman et al. |
| 6,726,651 | B1 | 4/2004 | Robinson et al. |
| 6,935,344 | B1 | 8/2005 | Aboul-Hosn et al. |
| 6,980,843 | B2 | 12/2005 | Eng et al. |
| 6,992,070 | B2 | 1/2006 | Donahue et al. |
| 7,211,073 | B2 | 5/2007 | Fitzgerald |
| 7,300,429 | B2 | 11/2007 | Fitzgerald et al. |
| 7,331,922 | B2 | 2/2008 | Mohl |
| 7,363,072 | B2 | 4/2008 | Movahed |
| 7,722,596 | B2 | 5/2010 | Shapland et al. |
| 8,152,786 | B2 | 4/2012 | Shapland et al. |
| 2001/0052345 | A1 | 12/2001 | Niazi |
| 2002/0062121 | A1 | 5/2002 | Tryggvason et al. |
| 2002/0099254 | A1 * | 7/2002 | Movahed ........................ 600/4 |
| 2002/0165598 | A1 | 11/2002 | Wahr et al. |
| 2003/0163081 | A1 | 8/2003 | Constantz et al. |
| 2003/0191434 | A1 | 10/2003 | Dorros et al. |
| 2003/0199917 | A1 * | 10/2003 | Knudson et al. .............. 606/200 |
| 2003/0236533 | A1 | 12/2003 | Wilson et al. |
| 2004/0002159 | A1 | 1/2004 | Xiao et al. |
| 2004/0030286 | A1 | 2/2004 | Altman |
| 2004/0099596 | A1 | 5/2004 | Naghavi et al. |
| 2004/0102732 | A1 | 5/2004 | Naghavi et al. |
| 2004/0102766 | A1 | 5/2004 | Poleo, Jr. |
| 2004/0210239 | A1 * | 10/2004 | Nash et al. .................... 606/127 |
| 2004/0254523 | A1 | 12/2004 | Fitzgerald et al. |
| 2005/0124969 | A1 | 6/2005 | Fitzgerald et al. |
| 2005/0226855 | A1 | 10/2005 | Alt et al. |
| 2005/0256441 | A1 | 11/2005 | Lotan et al. |
| 2006/0013772 | A1 | 1/2006 | LeWinter et al. |
| 2007/0078352 | A1 | 4/2007 | Pijls |
| 2007/0118072 | A1 | 5/2007 | Nash |
| 2007/0203445 | A1 | 8/2007 | Kaye et al. |
| 2007/0255162 | A1 | 11/2007 | Abboud et al. |
| 2008/0021314 | A1 * | 1/2008 | Movahed ...................... 600/431 |
| 2008/0108960 | A1 | 5/2008 | Shapland et al. |
| 2008/0306425 | A1 | 12/2008 | Al-Rashdan |
| 2009/0069829 | A1 | 3/2009 | Shturman |
| 2009/0234321 | A1 | 9/2009 | Shapland et al. |
| 2010/0041984 | A1 | 2/2010 | Shapland et al. |
| 2010/0082004 | A1 | 4/2010 | Shapland et al. |
| 2011/0015558 | A1 | 1/2011 | Kaye et al. |

FOREIGN PATENT DOCUMENTS

| | | |
|---|---|---|
| EP | 0 301 854 A2 | 2/1989 |
| EP | 0 150 960 B1 | 1/1990 |
| EP | 0 526 102 B1 | 4/1998 |
| GB | 2125487 A | 3/1984 |
| JP | 2001-526071 | 12/2001 |
| WO | WO 89/01309 | 2/1989 |
| WO | WO 92/20387 A1 | 11/1992 |
| WO | WO 98/31405 A | 7/1998 |
| WO | WO 98/56440 A | 12/1998 |
| WO | WO 99/06097 A | 2/1999 |
| WO | WO 99/29227 A1 | 6/1999 |
| WO | WO 99/30765 | 6/1999 |
| WO | WO 99/31982 | 7/1999 |
| WO | WO 01/00268 A | 1/2001 |
| WO | WO 01/13983 | 3/2001 |
| WO | WO 01/83004 A1 | 11/2001 |
| WO | WO 02/060511 A2 | 8/2002 |
| WO | WO 02/087677 A2 | 11/2002 |
| WO | WO 03/070330 A1 | 8/2003 |
| WO | WO 2005/027995 A2 | 3/2005 |
| WO | WO 2005/082440 | 9/2005 |
| WO | WO 2005/082440 A1 | 9/2005 |
| WO | WO 2006/004882 A1 | 1/2006 |
| WO | WO 2006/042219 A2 | 4/2006 |
| WO | WO 2007/002154 A | 1/2007 |
| WO | WO 2007/143288 A | 12/2007 |

OTHER PUBLICATIONS

Assali, A. et al., "Intracoronary Adenosine Administered During Percutaneous Intervention in Acute Myocardial Infarction and Reduction in the Incidence of "No Reflow" Phenomenon," *Catheterization and Cardiovascular Interventions*, vol. 51, pp. 27-31 (2000).

de Lemos, J. et al., "New tools for assessing microvascular obstruction in patients with ST elevation myocardial infarction," *Heart*, vol. 90, pp. 119-120 (2004).

Kramer, C., "The prognostic significance of microvascular obstruction after myocardial infarction as defined by cardiovascular magnetic resonance," *European Heart Journal*, vol. 26, pp. 532-533 (2005).

Marzilli, M. et al., "Primary coronary angioplasty in acute myocardial infarction: Clinical correlates of the 'no reflow' phenomonen," *International Journal of Cardiology*, vol. 65 (Suppl. 1), pp. S23-S28 (1998).

Resnic, F. et al., "No-reflow is an independent predictor of death and myocardial infarction after percutaneous coronary intervention," *American Heart Journal*, vol. 145, No. 1, pp. 42-46 (2003).

Office Action from related U.S. Appl. No. 11/510,203; dated Jan. 27, 2009; 10 pages.

Office Action from related U.S. Appl. No. 11/510,203; dated 06/22/09; 13 pages.

del Monte et al., "Improvement in Survival and Cardiac Metabolism After Gene Transfer of Sarcoplasmic Reticulum CA2+-ATPase in a Rat Model of Heart Failure", Circulation, 104(12): 1424-1429, 2001.

Hajjar et al., "Modulation of Ventricular Function Through Gene Transfer in Vivo", Proc. Natl. Acad. Sci., USA, 95: 5251-5256, 1998.

Logeart, D. et al., "How to Optimize In Vivo Gene Transfer to Cardiac Myocytes: Mechanical or Pharmacological Procedures?", Human Gene Therapy, 12: 1601-1610, 2001.

Michishita et al., "A Novel Contrast Removal System From the Coronary Sinus Using an Absorption Column During Coronary Angiography in a Porcine Model", Journal of the American College of Cardiology, vol. 47, No. 9, 2006.

Schrader, "Contrast Media-Induced Renal Failure: An Overview", Journal of Interventional Cardiology, vol. 18, No. 6, pp. 417-423, 2005.

Texas Heart Institute Journal, Transcatheter Coronary Artery Diagnostic Techniques, vol. 16, No. 3, 1989, 9 pgs.

\* cited by examiner

REGIONAL CARDIAC TISSUE TREATMENT

I. CROSS-REFERENCE TO RELATED APPLICATIONS

The present application is a continuation of U.S. application Ser. No. 11/490,476, filed Jul. 20, 2006 now U.S. Pat. No. 7,722,596; which is a continuation-in-part of International Application Serial No. PCT/AU2005/000237, filed Feb. 23, 2005; which application claims the benefit of U.S. Provisional Application Ser. No. 60/612,846, filed Sep. 24, 2004 and U.S. Provisional Application Ser. No. 60/548,038, filed Feb. 26, 2004; which applications are incorporated herein by reference.

II. BACKGROUND OF THE INVENTION

1. Field of the Invention

This invention pertains to methods and apparatus for treating tissue of a patient's heart. More particularly, this invention pertains to methods and apparatus for treating a region of heart tissue with therapeutic agents for treatment of microvascular obstructions. Also, the present invention pertains to treating an infarcted region of cardiac tissue.

2. Description of the Prior Art

The heart includes numerous coronary arteries for supplying oxygenated blood to the tissue of the heart. Occasionally, one or more of these coronary arteries may become fully or partially occluded. Upon such occurrence, the region of heart tissue served by the occluded vessel is deprived of oxygen.

If the occlusion occurs in a large vessel (e.g., a proximal portion of the left anterior descending artery, LAD), a large portion of the heart (e.g., the left side of the heart) is affected. If the occlusion occurs in a smaller vessel (e.g., a distal portion of the LAD or a branch of the LAD), a smaller region of heart tissue is affected.

The occlusion may progress to such a degree that the tissue in the region may become ischemic. Such ischemic tissue may revive after being re-supplied with an adequate flow of oxygenated blood. If left untreated and inadequately supplied with oxygenated blood, such tissue can become necrotic. Necrotic or infarcted tissue is a permanent injury to heart tissue. Such infarcted areas do not meaningfully participate in the pumping function of the heart. If the region of infarcted tissue is large enough, the patient may develop heart failure or die.

A patient with a coronary artery occlusion may have symptoms (such as chest pain) upon exertion. Location of an occlusion can be determined by an angiogram procedure. In such a procedure, a radiopaque dye is injected into the coronary arteries. The heart is inspected under fluoroscopy and the location of the occlusion is noted.

An occlusion can be treated in a number of different ways. Interventional treatments include surgery and percutaneous treatments. In surgery, a harvested blood vessel is attached to the occluded coronary artery distal to the occlusion. Percutaneous procedures include, among others, balloon angioplasty and stenting. In angioplasty, a balloon is placed in the artery in the region of the occlusion. Expansion of the balloon opens the occlusion. Stenting is similar differing in that a stent (e.g., a metal cage) is left in place at the site of the occlusion.

Intervention can greatly improve a patient's condition. However, a significant number of patient's continue to experience symptoms consistent with occlusion after such intervention. One cause of such persistent symptoms is believed to be microvascular obstruction. In such patients, the microvasculature of the heart (e.g., the arterioles and the capillaries at which the oxygen-carbon dioxide exchange occurs) is occluded with microscopic obstructions.

Microvascular obstruction is common in post-myocardial infarction patients. "In fully 25% of patients in whom arterial obstruction is successfully relieved, little to no additional myocardial perfusion results. These patients . . . exhibit a substantial increase in overall morbidity and mortality." Alfayoumi, F., et al., "The No-Reflow Phenomenon: Epidemiology, Pathophysiology, and Therapeutic Approach", *Reviews in CV Medicine*, Vol 6, No 2, p 72-83 (2005). The frequency of microvascular obstruction is up to 44% in patients undergoing primary interventions for acute myocardial infarction. Marzilli M., et al., "Primary Coronary Angioplasty in Acute Myocardial Infarction: Clinical Correlates of the 'No Reflow' Phenomenon", *International J. of Cardiology*, Vol. 65 (Suppl. 1) pp. S23-S28 (1998). Assali, A R., et al., "Intracoronary Adenosine Administered During Percutaneous Intervention in Acute Myocardial Infarction and Reduction in the Incidence of 'No Reflow' Phenomenon", *Catheter Cardiovasc Interv*, Vol. 51, No. 1, pp. 27-31 (2000).

Microvascular obstruction is associated with very serious negative prognosis with profound clinical consequences including heart failure. Persistent microvascular obstruction is a more powerful predictor of survival than infarct size and a high risk factor for late ventricular remodeling. Kramer, C. M., "The Prognostic Significance of Microvascular Obstruction after Myocardial Infarction as Defined by Cardiovascular Magnetic Resonance", *European Heart Journal*, Vol. 26, pp. 532-533 (2005). " . . . [T]he risk of subsequent major adverse events [is] as much as 10 times higher in the no-reflow population than in historical control patients." Resnic, F S., et al., "No-Reflow is an Independent Predictor of Death and Myocardial Infarction after Percutaneous Intervention", *American Heart J*, Vol. 145, No. 1, pp. 42-46 (2003).

Currently, treatment options for microvascular obstruction are limited and of generally inadequate effectiveness. Such treatments include systemic infusion of vasodilators, anti-platelet, and anti-thrombin agents. These treatments have produced disappointing results. Treatment options for ischemia are also limited. These include regional blood flow augmentation and treatment for enhanced function. Such treatments include delivery of angiogenic agents to encourage new vessel growth and cell delivery to improve function.

More recently developed treatments for microvascular obstruction include intracoronary injection of therapeutic agents to treat the microvascular occlusion. These agents include vasodilators (adenosine, verapamil, nitroprusside) and anti-platelet agents (IIb/IIIa). These treatments show some promise. However, these treatments are supported by only very limited studies. Also, such treatments have the potential for systemic toxicity.

It is an object of the present invention to provide a treatment for microvascular obstruction in a region of a patient's heart and treatment of regional myocardial ischemia.

III. SUMMARY OF THE INVENTION

According to a preferred embodiment of the present invention, a method is disclosed for treating an occlusion in a coronary artery of a patient. The method includes percutaneously advancing an occlusion treatment tool through the vasculature of the patient and into a coronary artery to a site of the occlusion. The tool may be any suitable treatment such as an angioplasty balloon or stent delivery. The occlusion is treated with the occlusion treatment tool. Following the treatment of the occlusion, one or more therapeutic agents are admitted (either simultaneously or sequentially in the case of multiple agents) to the first coronary artery with the therapeutic agent. The therapeutic agent is selected to treat microvasculature obstructions at a target cardiac tissue site distal to the site of the occlusion. Suitable therapeutic agents include anti-thrombin agents, anti-platelet agents, anti-spasm agents and thrombolytic agents. At least a portion of a blood flow is withdrawn from a coronary vein distal to the cardiac tissue site. Additional embodiments include oxygenating the blood flow withdrawn from the coronary vein and returning the oxygenated blood flow to the coronary artery. Also, a similar treatment for ischemia or infarction is disclosed.

V. DESCRIPTION OF A PREFERRED EMBODIMENT

With reference now to the various drawing figures in which identical elements are numbered identically throughout, a description of the preferred embodiment of the present invention will now be described.

As will be more fully described, the present invention is most preferably used in concert with a percutaneous treatment for an occluded coronary artery. In such use, the present invention may be used to prevent formation of micro obstructions in tissue distal to the obstruction or to treat preexisting micro obstructions in such tissue. Further, the present invention may be used as an independent therapy to treat or prevent micro obstructions of coronary tissue and to treat infarcted tissue regions. Most of the following description describes the invention in an embodiment for treatment of microvascular obstructions. However, the principles and techniques described are also applicable to treating regional ischemia or infarction. Specifics of such treatments are later described.

Figure 1:
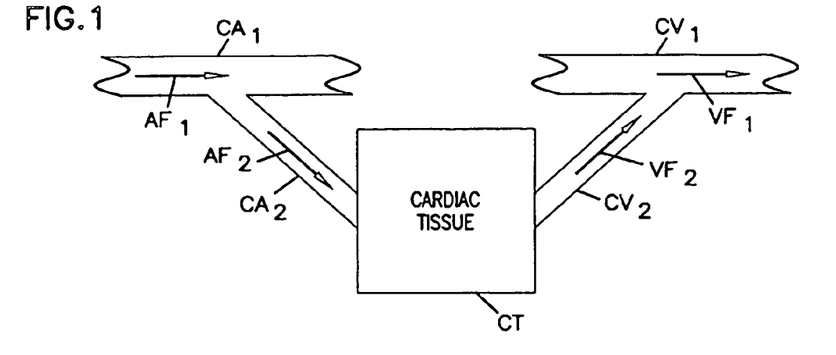
FIG. 1 is a schematic representation of a target region of cardiac tissue to be treated and showing a major coronary artery and a smaller branch coronary artery for supplying oxygenated blood to the region and a major coronary vein and a tributary coronary vein for directing blood from the region back to the right atrium of the heart.

With initial reference to FIG. 1, a target cardiac tissue CT is schematically shown and labeled. The target cardiac tissue CT is tissue known or suspected to contain micro-obstructions within the capillaries of the tissue or other impairment to flow within the capillaries.

Oxygenated blood flow to the target tissue CT is shown provided by a branch coronary artery $CA_2$ having a normal arterial blood flow rate of $AF_2$. The branch coronary artery $CA_2$ receives blood from a major coronary artery $CA_1$ having an arterial blood flow rate $AF_1$. It will be appreciated flow rate $AF_1$ is greater than flow rate $AF_2$. The remainder of the blood flow (i.e., $AF_1$ minus $AF_2$) is supplied by the major coronary artery $CA_1$ to other cardiac tissue (not shown).

By way of representative example, the major coronary artery $CA_1$ could be the patient's main coronary artery or other major coronary artery (such as the right coronary artery or the left anterior descending coronary artery). The branch coronary artery $CA_2$ could be any artery branching off of the major coronary artery. Further, and by way of non-limiting example, a left anterior descending artery may have a flow rate of about 100 milliliters per minute (mL/min). A branch artery may have a flow rate of about 30 mL/min. It will be appreciated such rates vary from patient to patient and, for any given patient, vary throughout the day.

Within the target tissue, oxygen from the blood flow of the branch coronary artery $CA_2$ is exchanged with carbon dioxide through the capillaries (not shown) in the target tissue CT. After such exchange, blood flow is returned to the heart by the blood first flowing through a tributary coronary vein $CV_2$ into a major coronary vein $CV_1$ for ultimate delivery to the right atrium (not shown) of the patient. The flow rate $VF_2$ in the tributary coronary vein $CV_2$ is less than the blood flow rate $VF_1$ in the major coronary vein $CV_1$.

The present invention delivers a therapeutic agent to the target tissue CT while substantially isolating the remainder of the cardiac tissue from such agent. This isolation permits delivery of the therapeutic agent only to the target tissue CT and avoids or minimizes delivery of such agent to the remainder of the tissue of the patient's heart. Further, the present invention avoids delivery of such therapeutic agent systemically to the patient. As a result, a higher dose of the therapeutic agent may be applied to the target tissue than would otherwise be possible for safe delivery of such agent if delivered systemically or if delivered to the entire heart.

Figure 2:
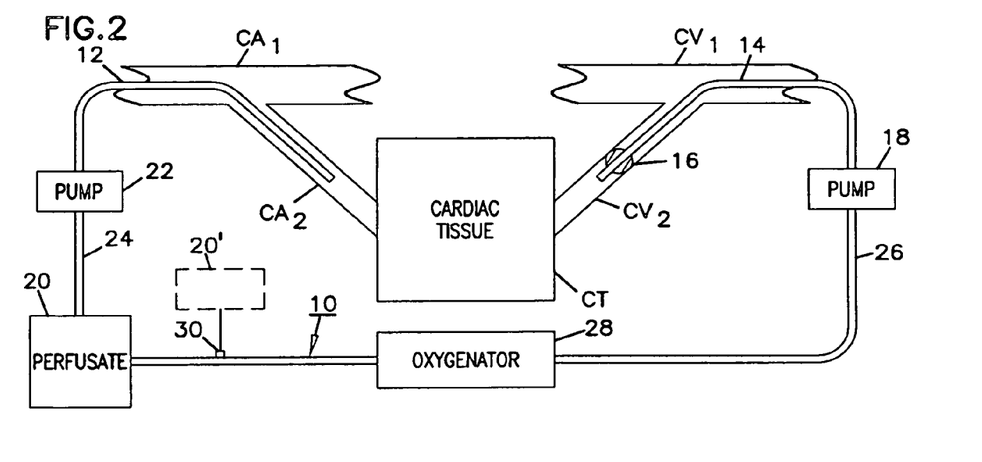
FIG. 2 is the view of FIG. 1 showing a perfusion catheter in the branch coronary artery and showing a collection catheter in the tributary coronary vein and showing a perfusion circuit.

FIG. 2 illustrates a circuit 10 for isolated delivery of a therapeutic agent to the target cardiac tissue CT. A perfusion catheter 12 is shown passed through the major coronary artery $CA_1$ and into the branch coronary artery $CA_2$. A collection catheter 14 is shown passed through the major coronary vein $CV_1$ and into the tributary coronary vein $CV_2$. The collection catheter 14 has an inflatable balloon 16 at its distal end which may be inflated within the tributary coronary vein $CV_2$. As a result, all blood flow $VF_2$ flows into the collection catheter 14.

Components for the circuit 10 (e.g., perfusion and collection catheters, oxygenators and pumps) are described in commonly assigned International Patent Application Ser. No. PCT/AU2005/000237 filed Feb. 23, 2005 and published Sep.

9, 2005 as International Publication No. WO 2005/082440 A1 (incorporated herein by reference).

In FIG. 2, a reservoir of a perfusate is shown at 20. The perfusate can be any therapeutic agent selected for preventing formation of microvascular obstructions or to treat existing micro obstructions. By way of non-limiting example, suitable agents for use in the invention are anti-thrombin agents, anti-platelet agents, anti-spasm agents and thrombolytic agents. Numerous ones of such agents already enjoy approval by the U.S. Food and Drug Administration (FDA) for various indications and with established dosage guidelines.

Examples of such anti-thrombin agents include (names in parenthesis are trade names): Bivalirudin (Angiomax), Hirudin (Refludan), low molecular weight heparin such as Dalteparin (Fragmin), low molecular weight heparin such as Enoxaparin (Lovenox), Heparin. Examples of such anti-spasmodic agents include: Adenosine (Adenocard IV), Verapamil HCl, Nitro glycerin, Nitropusside, Lidocanine. Examples of such anti-platelet agents include abciximab (ReoPro) IIb/IIIa, Eptifibatide (Integrilin) IIb/IIIa, Tirofiban (Aggrastat) IIb/IIIa. Examples of such thrombolytic agents include Streptokinase, Anistreplase (Eminase), Alteplase or tPA (Activase), Reteplase (Retavase), Tecnecteplase (TNKase).

A delivery pump 22 draws the perfusate 20 through tubing 24 and delivers the perfusate to the perfusate catheter 12. Tubing 26 connects the output of the collection pump 18 to an oxygenator 28. The oxygenator 28 can be any commercially available unit for exchanging oxygen for carbon dioxide contained within blood. In the embodiment of FIG. 2, the perfusate reservoir receives blood from the oxygenator 28 for recirculation through the circuit 10.

As an alternative to the embodiment thus described, the pump 22 and reservoir 20 can be eliminated with blood delivered from the oxygenator directly to the perfusate catheter 12. Instead, perfusate could be added to the tubing 10 through needle injection or IV-drip or the like from a reservoir 20' (shown in phantom lines) into a port 30.

With the embodiment of FIG. 2, a higher dose of the perfusate than could otherwise be administered safely through systemic delivery or delivery to the entire heart of the patient is administered directly and only to the target tissue region CT.

Figure 3:
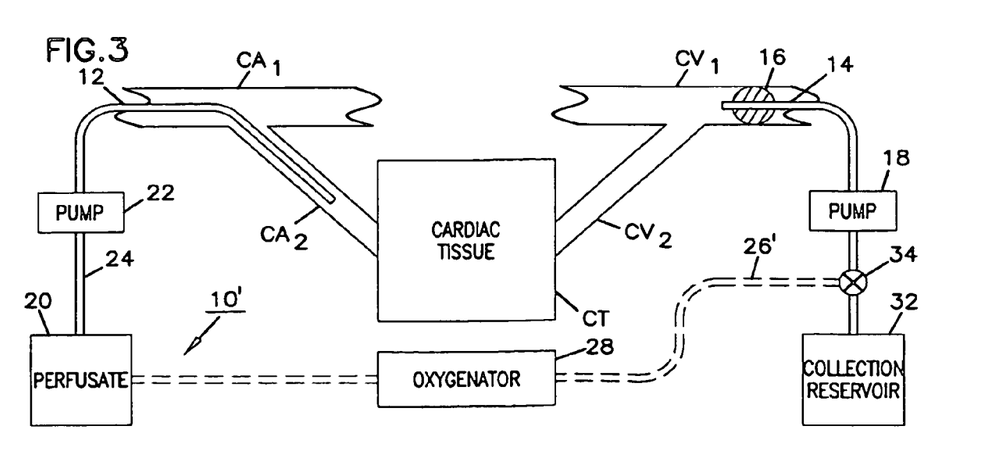
FIG. 3 is the view of FIG. 1 showing a perfusion catheter in the branch coronary artery and showing a collection catheter in the major coronary vein and showing a perfusion circuit.

In the embodiment of FIG. 3, the blood flow rate in the branch coronary artery $CA_2$ is assumed to be approximate to the blood flow rate in the tributary coronary vein $CV_2$. In practice, it may not be possible to place the collection catheter 14 in a small enough coronary vein having a flow rate comparable to the flow rate in the coronary artery in which the perfusate catheter 12 resides. This is illustrated as an alternative circuit 10' in FIG. 3.

In FIG. 3, the perfusate catheter 12 is placed within the branch coronary artery $CA_2$ as in the embodiment of FIG. 2. However, FIG. 3 assumes that the collection catheter 14 cannot be safely or conveniently placed within a tributary coronary vein $CV_2$ having a flow rate comparable to the flow rate of the branch coronary artery $CA_2$. Instead, the collection catheter 14 is placed within a larger coronary vein $CV_1$ having a greater flow rate.

Since the collection catheter 14 collects all of the blood flow from the major coronary vein $CV_1$, such blood flow cannot be re-circulated back into the branch coronary artery $CA_2$. Accordingly, the blood collected in the collection catheter 14 is pumped into a collection reservoir 32. The blood within the reservoir 32 can be collected and later discarded. It is generally recognized that blood amounts less than 250 milliliters may be safely removed from a patient. Such blood flow loss is anticipated to be small since it is anticipated that the delivery of perfusate by the perfusate catheter 12 will occur for only a short period of time (for example five to ten minutes) for a therapeutic treatment.

In lieu of discarding the blood, it may be treated to remove or reduce the perfusate in the blood. So treated, the blood may be returned (with or without oxygenation) to catheter 12. Such treatments may include filtering the blood, spinning the blood to collect and return the blood as packed cells or treating the blood with serum/clotting factors or other cleansing treatments including dialysis.

Alternatively, a portion of the blood flow from the collection catheter 14 (matching the flow rate in the branch coronary artery $CA_2$) can be returned through an oxygenator 28 into the perfusate reservoir 20. In FIG. 3, this diverted flow is illustrated by the dotted line tube 26'. The flow is diverted by a flow control valve 34.

Figure 4:
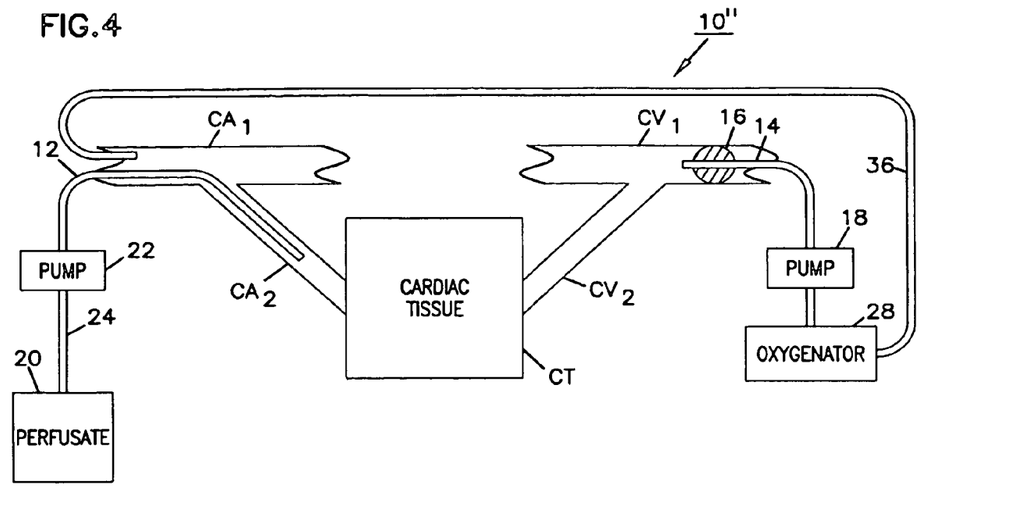
FIG. 4 is the view of FIG. 3 showing an alternative perfusion circuit.
Figure 5:
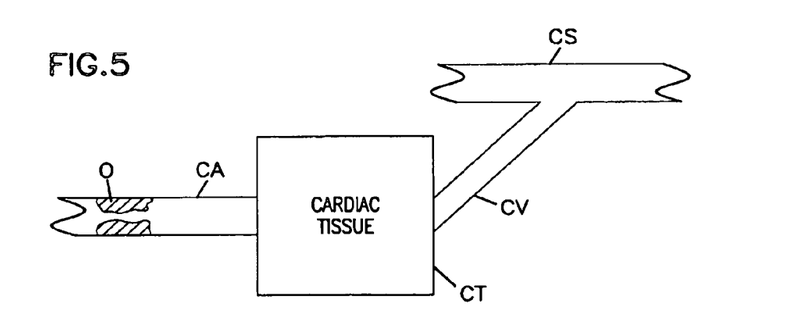
FIG. 5 is a schematic showing of cardiac tissue receiving a supply of oxygenated blood from a coronary artery with blood flow from the region through a coronary vein and into a larger coronary vein such as the coronary sinus and showing an occlusion at least partially blocking blood flow through the coronary artery.

FIG. 4 illustrates a still further alternative circuit 10". In FIG. 4, blood flow from the collection catheter 14 is passed through an oxygenator 28 into a catheter 36 for delivery to the major coronary artery $CA_1$. While the blood delivered to the major artery contains the perfusate, it is diluted within the major artery. Further, such perfusate is kept from circulating to other organs (such as the liver).

In FIG. 4, the perfusate reservoir can be an IV bag or syringe with the perfusate administered directly to the catheter 12 without a need for pump 22.

Figure 9:
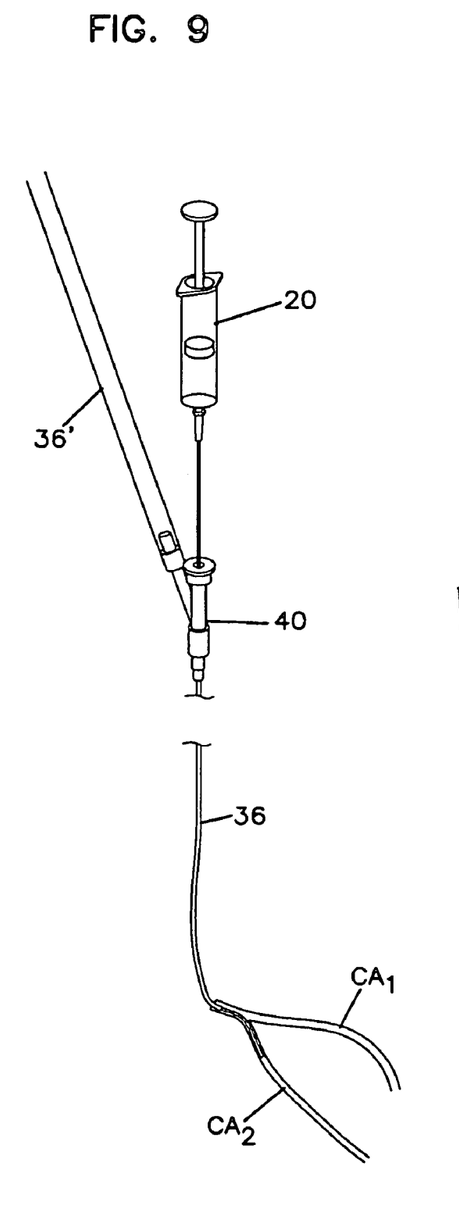
FIG. 9 is a view of a catheter for use in the present invention.
Figure 10:
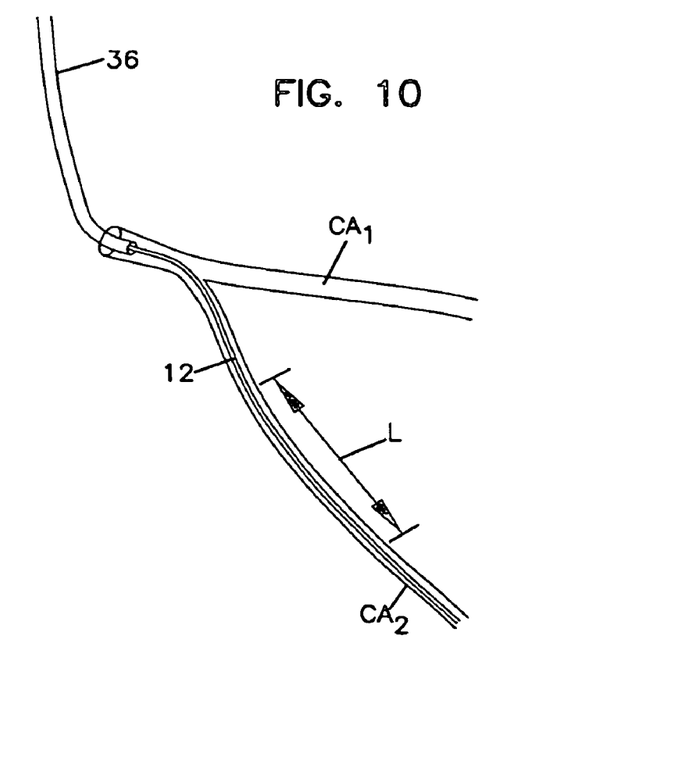
FIG. 10 is an enlarged view of a distal end of the catheter of FIG. 9.

FIGS. 9 and 10 illustrate a catheter system for use in the embodiment of FIG. 4. The catheter 36 includes a portion 36' connected to the output of the oxygenator of FIG. 4. At a couple 40, the perfusion catheter 12 is received within the lumen of catheter 36. At the coupling 40, the perfusion reservoir 20 (a syringe injection in FIG. 9) admits perfusate to the catheter 12. Catheter 36 resides within the major coronary artery $CA_1$. Catheter 12 extends from catheter 36 into the branch coronary artery $CA_2$. The distal end of catheter 12 may be closed or open. In either event, catheter 12 preferably has a plurality of holes through its side wall along a length L (e.g., five centimeters) for delivery of the perfusate into the branch coronary artery $CA_2$.

As mentioned earlier, the present invention is preferably used in concert with a procedure for treating an obstruction in a coronary artery. This procedure is illustrated schematically in FIGS. 5-8.

Figure 6:
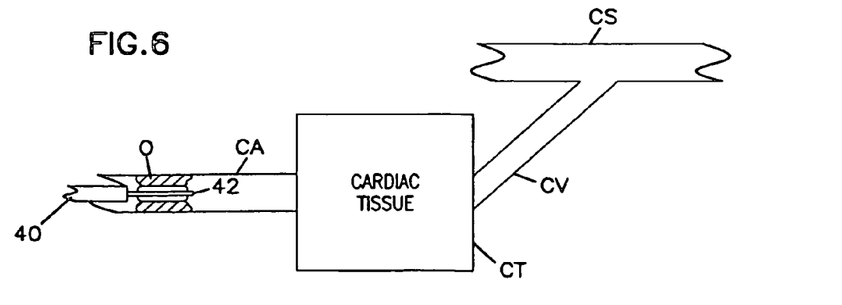
FIG. 6 is the view of FIG. 5 showing an occlusion treatment tool passed into the coronary artery through a delivery catheter.

In FIG. 6, coronary artery CA is shown supplying blood to a region of cardiac tissue CT. Blood flow from the tissue CT passes through a coronary vein CV and into a larger coronary vein CS (for example, the coronary sinus) for ultimate delivery to the right atrium of the heart. The coronary artery CA contains an occlusion O at least partially blocking blood flow to the tissue region CT.

FIG. 6 shows a delivery catheter 40 passed into the coronary artery CA to a site proximal to the obstruction O. An obstruction treatment tool 42 is passed through the catheter 40 with the tool 42 positioned to treat the obstruction O. The tool 42 and treatment method for treating the obstruction may be any tool or treatment known in the prior art. Such tools include, by way of non-limiting example, expandable balloons for angioplasty procedures, stent delivery catheters for delivering a stent to the location of the obstruction or atherectomy devices for breaking up and removing an obstruction or localized delivery of agents to dissolve the obstruction.

Figure 7:
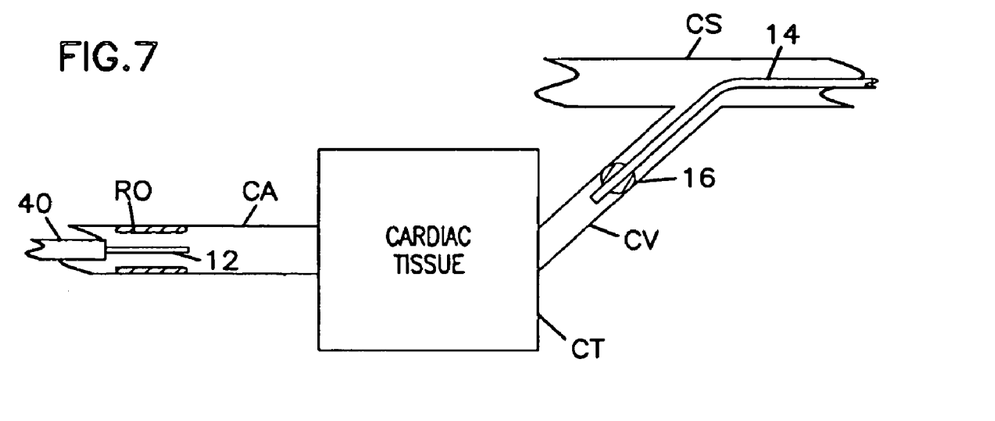
FIG. 7 is the view of FIG. 6 following treatment of the occlusion and showing a perfusion catheter admitted to the coronary artery through the delivery catheter and showing a collection catheter in the coronary vein.

Following treatment, the obstruction is reduced in size or eliminated as illustrated by the reduced occlusion RO in FIG. 7. After such treatment, the guide catheter 40 may then be used to guide the perfusion catheter 12 into the coronary artery CA as illustrated in FIG. 7.

In FIG. 7, the collection catheter 14 is placed within the coronary vein CV and occludes the vein with the balloon 16 to collect all of the blood flow from the coronary vein. Incomplete occlusion (e.g., use of a collection catheter 14 without balloon 16) is acceptable as long as the amount of therapeutic agent in the remainder flow (i.e., total flow in vein CV less the diverted flow to catheter 14) remains within clinically acceptable levels for systemic delivery.

Figure 8:
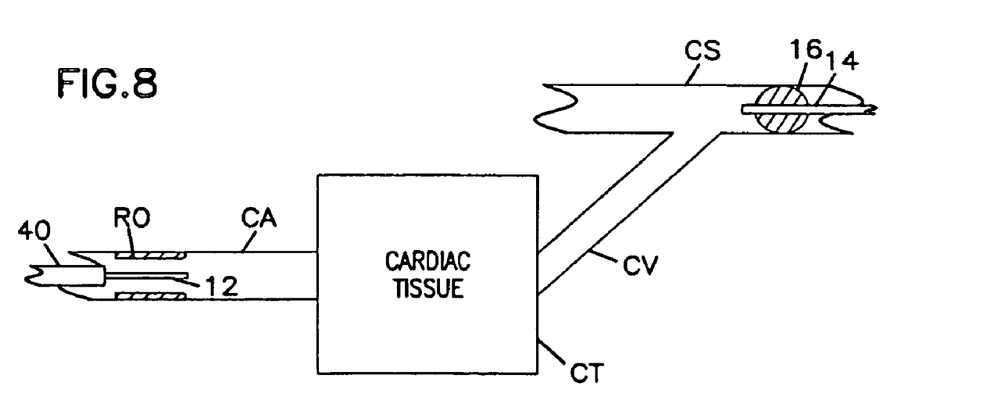
FIG. 8 is the view of FIG. 7 showing the collection catheter in the coronary sinus.

In FIG. 7, the circuit for the delivery of the perfusate to the perfusion catheter 12 and the collection of the blood from the coronary vein will be the same as disclosed and described with reference to FIG. 2. In the event the collection catheter 14 cannot be placed within a vein CV having a blood flow comparable to that of the blood flow in the coronary artery CA, the collection catheter 14 can be placed in a larger coronary vein (such as the coronary sinus CS) as illustrated in FIG. 8. The balloon 16 occludes the coronary sinus CS to collect the entire blood flow of the coronary sinus CS which will include the blood flow from the target region CT. As described in reference to FIG. 7, partial occlusion of the coronary sinus CS is acceptable as long as the amount of therapeutic agent in the non-diverted flow is deemed safe for systemic delivery.

The complete circuit for the treatment of FIG. 8 may be such as that illustrated and described with reference to FIG. 3. The circuitry of FIG. 4 can used if it is desired to admit the therapeutic agent to a branch artery of the originally occluded artery or if desired to admit the therapeutic agent in a main artery of which the occluded artery is a branch.

Throughout the above, different catheters or other tools have been shown, described and separately numbered for performing certain functions. For example, tools 50, 52 and 12 are separately shown and described. It will be appreciated these functions can be performed with a single catheter avoiding the need for multiple catheter replacements.

A microvascular obstruction treatment as described can be used in any percutaneous occlusion treatment as a precaution against known or suspected microvascular obstructions in tissue distal to the occlusion. More preferably, the likelihood of such microvascular obstructions is first assessed before applying the microvascular obstruction treatment.

Figure 6A:
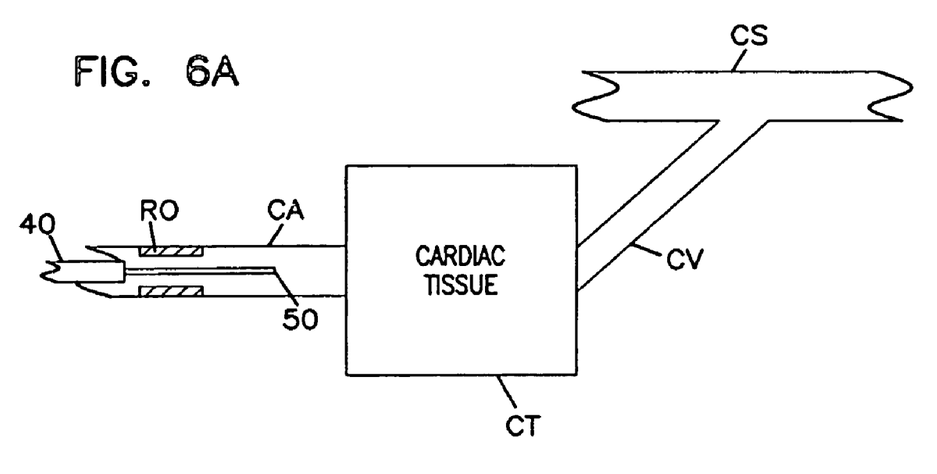
FIG. 6A is the view of FIG. 6 showing an intermediate procedure for assessing regional perfusion including determining the presence of microvascular obstructions in the cardiac tissue.
Figure 6B:
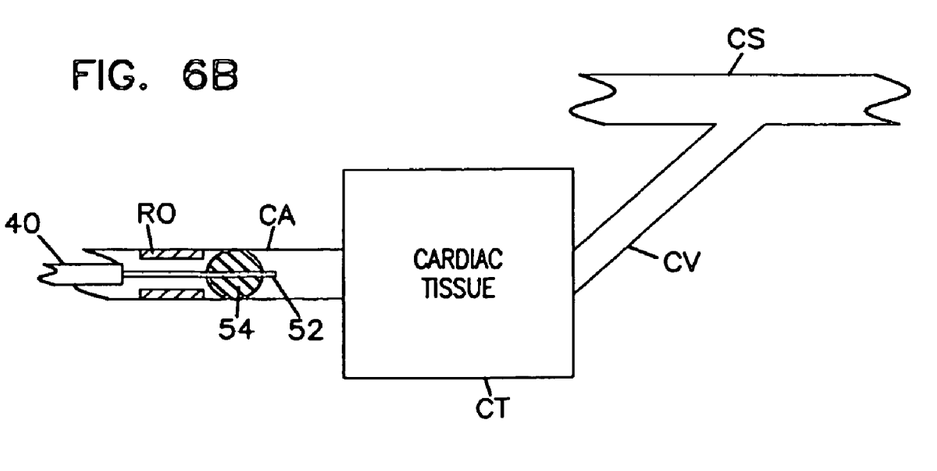
FIG. 6B is the view of FIG. 6 showing an alternative intermediate procedure for assessing regional perfusion including determining the presence of microvascular obstructions in the cardiac tissue.

FIGS. 6A and 6B illustrate intermediate assessment techniques. In FIG. 6A, a flow rate measurement tool 50 is passed through the delivery catheter 40 after treatment of the occlusion as described with reference to FIG. 6. The characteristics of the measured flow rate in the coronary artery indicate the likelihood of microvascular obstructions in the cardiac tissue CT. For example, a low- or no-flow condition following treatment of the occlusion O indicates the presence of such microvascular obstructions. In FIG. 6B, the assessment tool is a pressure sensor 52 distal to an occluding balloon 54. Pressure parameters (such as absolute pressure or pressure waveform) indicate the likelihood of microvascular obstructions in the cardiac tissue CT. Assessment of microvascular obstructions through such techniques is described in Lemos, et al., "New Tools for Assessing Microvascular Obstruction in Patients with ST Elevation Myocardial Infarction", *Heart*, Vol. 90, pp. 119-120 (2004).

The assessment procedures may also be performed throughout the admission of the therapeutic agent to the artery. For example, if a treatment procedure is planned to last 10 minutes, it may be discontinued early in the event an assessment procedure indicates faster effective treatment has occurred.

While the foregoing invention has been described with reference to placing catheters in a single coronary artery, multiple coronary arteries can be treated with delivery catheters and where the blood flow is collected in one or more collection catheters (e.g., delivery to the right coronary artery and the left anterior descending artery with a single collection through the coronary sinus).

With the present invention, an occluded artery is treated to correct the occlusion. The microvascular obstruction therapy of the present invention is then applied. Preferably, the therapy is applied immediately after the occlusion treatment while the patient is still in the catheter lab and the guide catheter 40 is in place. The perfusion circuit 10, 10' or 10" can operate for a time (e.g., 15 minutes at a delivery rate of 50-100 mL/min., by way of non-limiting example) to more thoroughly treat the patient and reduce risks otherwise associated with microvascular obstruction.

The present invention is also useful for treating infarcted cardiac tissue. In treatment of an infarcted tissue region, the perfusion catheter is placed in a coronary artery perfusing substantially only the infarcted tissue region. The collection catheter may be placed in any coronary vein such as the coronary sinus, distal to the infarcted region. Treatment (such as oxygenation) and return of the collected blood can be according to any of the embodiments described above. The perfusate is a therapeutic agent selected for treatment of infarcted tissue regions. Such agents include angiogenetic agents to promote new vessel growth, agents to promote new myocardial cell growth, agents to prevent fibrosis, and other agents to minimize the infarct size and or degree of dysfunctional. Such agents could be delivered in the form of proteins, gene based agents or cells, such as but not limited to stem cells. One of ordinary skill in the art will readily recognize various agents within these categories.

With the foregoing detailed description of the present invention, it has been shown how the objects of the invention have been attained in a preferred manner. Modifications and equivalents of disclosed concepts such as those which might readily occur to one skilled in the art are intended to be included in the scope of the claims which are appended hereto. For example, the present invention can be applied to organs other than the heart to treat a region of the organ.

What is claimed is:

1. A method of treating a region of cardiac tissue of an unarrested heart, wherein the region of cardiac tissue is suspected to be inflicted with a microvascular obstruction, the method comprising the steps of:
    positioning a perfusate catheter into a coronary artery so as to allow blood flow from the unarrested heart through the coronary artery to the region of cardiac tissue of the unarrested heart;
    allowing pulsatile blood flow to the region of cardiac tissue of the unarrested heart;
    perfusing the region of cardiac tissue of the unarrested heart, including administering a therapeutic agent to the region of cardiac tissue, the therapeutic agent being selected to treat microvascular obstructions; and
    systemically isolating the administered therapeutic agent by withdrawing the agent prior to systemic circulation by the unarrested heart, wherein the isolating step includes positioning a collection catheter into the coronary venous system and applying suction to the collection catheter.

2. The method of claim 1, wherein the step of systemically isolating the administered therapeutic agent includes withdrawing the therapeutic agent at a location distal to the region of cardiac tissue.

3. The method of claim 1, wherein the region of cardiac tissue is distal to a cardiac occlusion location.

4. The method of claim 3, further including treating an occlusion at the cardiac occlusion location prior to perfusing the region of cardiac tissue.

5. The method of claim 4, further including advancing an occlusion treatment tool through a patient's vasculature and into a coronary artery toward the cardiac occlusion location.

6. The method of claim 1, further including placing a perfusion catheter into a patient's coronary artery and placing a collection catheter into the patient's coronary vein.

7. The method of claim 1, wherein the step of systemically isolating includes withdrawing the therapeutic agent and an amount of blood.

8. The method of claim 7, further including admitting the withdrawn blood back into the patient's vasculature.

9. The method of claim 8, further including oxygenating the withdrawn blood prior to admitting the withdrawn blood back into the patient's vasculature.

10. The method of claim 7, further including discarding the withdrawn blood.

11. The method of claim 7, further including diverting a portion of the withdrawn blood, oxygenating the diverted portion of withdrawn blood, and admitting the diverted, oxygenated, withdrawn blood back into the patient's vasculature.

12. The method of claim 1, furthering including assessing the region of cardiac tissue for microvascular obstructions.

13. The method of claim 12, wherein the step of assessing includes obtaining feedback from a flow rate measurement tool placed within a patient's coronary artery.

14. The method of claim 12, wherein the step of assessing includes obtaining feedback from a pressure sensor placed within a patient's coronary artery.

15. A method of treating a region of cardiac tissue of an unarrested heart, wherein the region of cardiac tissue is suspected to be inflicted with a microvascular obstruction, the method comprising the steps of:

positioning a perfusate catheter into a coronary artery so as to allow blood flow from the unarrested heart through the coronary artery to the region of cardiac tissue of the unarrested heart;

allowing pulsatile blood flow to the region of cardiac tissue of the unarrested heart;

perfusing the region of cardiac tissue of the unarrested heart, including administering a therapeutic agent to the region of cardiac tissue of the unarrested heart, the therapeutic agent being selected to treat microvascular obstructions; and monitoring the region after perfusion of the region for microvascular obstructions, wherein the monitoring step includes advancing an assessment tool into a patient's coronary artery and obtaining feedback from the unarrested heart.

16. The method of claim 15, wherein the assessment tool includes a flow rate measurement device that is advanced into the patient's coronary artery.

17. The method of claim 15, wherein the assessment tool includes a pressure sensor that is advanced into the patient's coronary artery.

18. The method of claim 15, further including systemically isolating the administered therapeutic agent by withdrawing the agent prior to systemic circulation by the unarrested heart.

19. The method of claim 18, wherein the step of systemically isolating includes withdrawing the therapeutic agent and an amount of blood.

20. The method of claim 15, further including treating an occlusion at a cardiac occlusion location prior to perfusing the region of cardiac tissue, the cardiac occlusion location being proximal to the region of cardiac tissue.

* * * * *